United States Patent
Stone et al.

(10) Patent No.: US 10,463,249 B1
(45) Date of Patent: *Nov. 5, 2019

(54) COMPREHENSIVE OCULOMOTOR BEHAVIORAL RESPONSE ASSESSMENT SYSTEM

(71) Applicant: UNITED STATES OF AMERICA AS REPRESENTED BY THE ADMINISTRATOR OF NASA, Washington, DC (US)

(72) Inventors: Leland Stone, San Francisco, CA (US); Dorion Liston, Boulder Creek, CA (US)

(73) Assignee: United States of America as Represented by the Administrator of NASA, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/676,875

(22) Filed: Aug. 14, 2017

Related U.S. Application Data

(62) Division of application No. 14/710,260, filed on May 12, 2015, now Pat. No. 9,730,582.

(Continued)

(51) Int. Cl.
*A61B 3/00* (2006.01)
*A61B 3/032* (2006.01)
*A61B 3/113* (2006.01)

(52) U.S. Cl.
CPC ............ *A61B 3/113* (2013.01); *A61B 3/0025* (2013.01); *A61B 3/0041* (2013.01); *A61B 3/0091* (2013.01); *A61B 3/032* (2013.01)

(58) Field of Classification Search
CPC ..... A61B 3/113; A61B 3/0041; A61B 3/0091; A61B 3/032; A61B 3/0025; A61B 3/02
(Continued)

(56) References Cited

U.S. PATENT DOCUMENTS 9,730,582 B1 * 8/2017 Stone ............... A61B 3/113
2014/0313488 A1 * 10/2014 Kiderman ......... A61B 3/145
351/246

(Continued)

*Primary Examiner* — Jordan M Schwartz
(74) *Attorney, Agent, or Firm* — Rhys W. Cheung; Robert M. Padilla

(57) ABSTRACT

An eye movement-based methodology and assessment tool may be used to quantify many aspects of human dynamic visual processing using a relatively simple and short oculomotor task, noninvasive video-based eye tracking, and validated oculometric analysis techniques. By examining the eye movement responses to a task including a radially-organized appropriately randomized sequence of Rashbass-like step-ramp pursuit-tracking trials, distinct performance measurements may be generated that may be associated with, for example, pursuit initiation (e.g., latency and open-loop pursuit acceleration), steady-state tracking (e.g., gain, catch-up saccade amplitude, and the proportion of the steady-state response consisting of smooth movement), direction tuning (e.g., oblique effect amplitude, horizontal-vertical asymmetry, and direction noise), and speed tuning (e.g., speed responsiveness and noise). This quantitative approach may provide fast and results (e.g., a multi-dimensional set of oculometrics and a single scalar impairment index) that can be interpreted by one without a high degree of scientific sophistication or extensive training.

20 Claims, 10 Drawing Sheets

Related U.S. Application Data

(60) Provisional application No. 61/994,673, filed on May 16, 2014.

(58) Field of Classification Search
USPC .............. 351/209, 210; 382/103; 600/558; 345/156, 157
See application file for complete search history.

(56) References Cited

U.S. PATENT DOCUMENTS

| | | | |
|---|---|---|---|
| 2015/0282705 A1* | 10/2015 | Avital | A61B 3/113 600/301 |
| 2016/0367165 A1* | 12/2016 | Khaderi | A61B 3/113 |
| 2017/0007119 A1* | 1/2017 | Cornsweet | A61B 3/113 |

\* cited by examiner

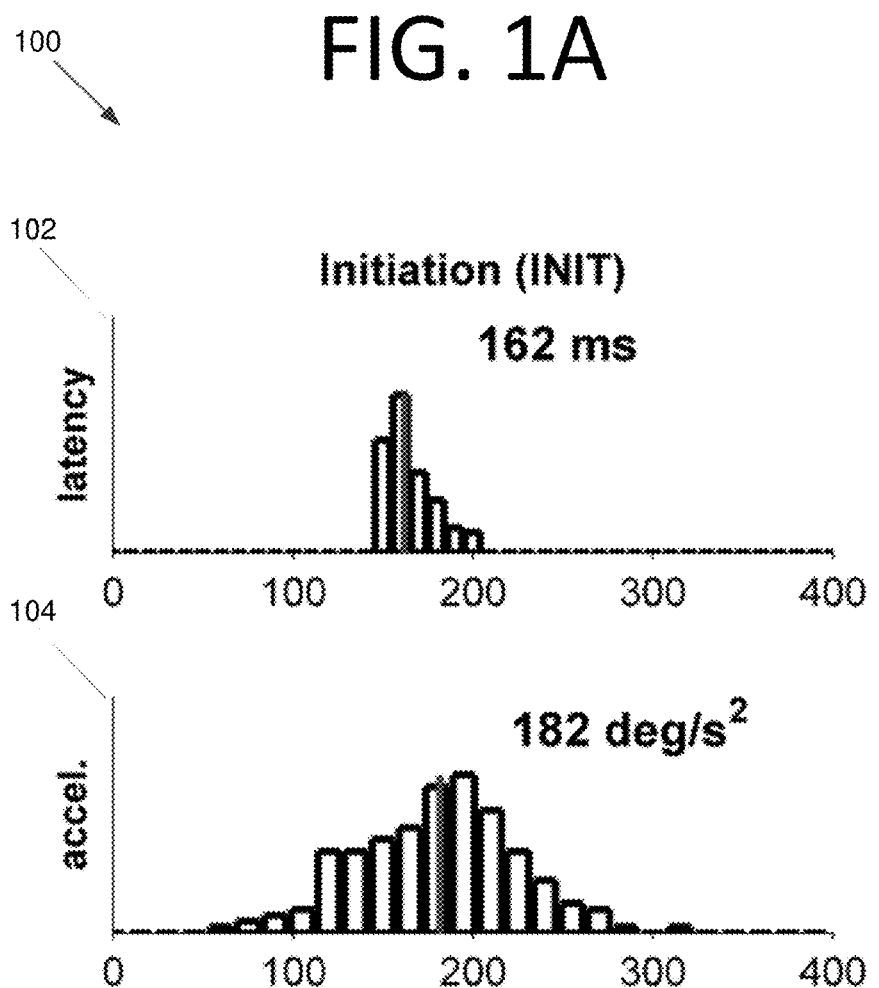

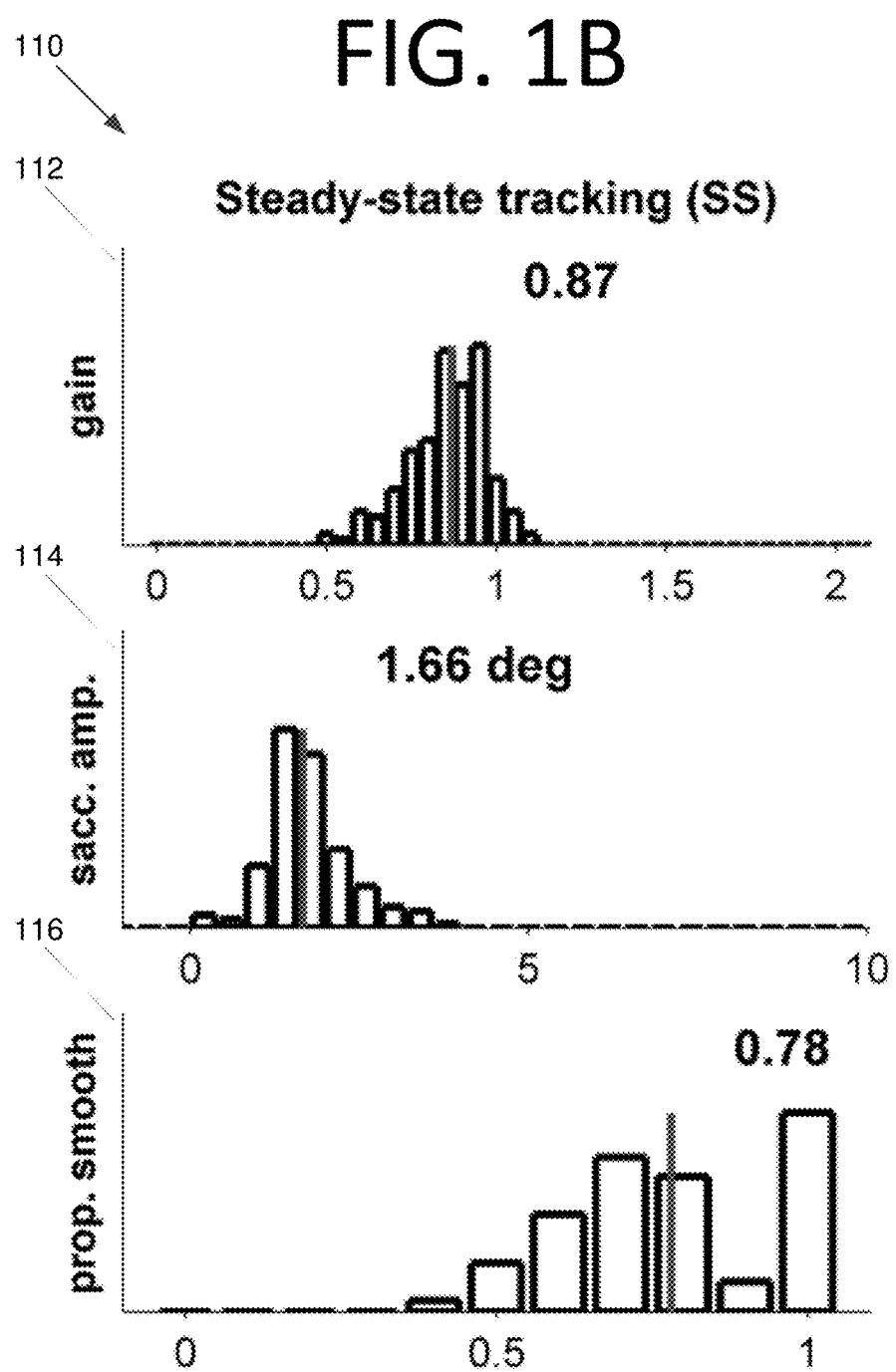

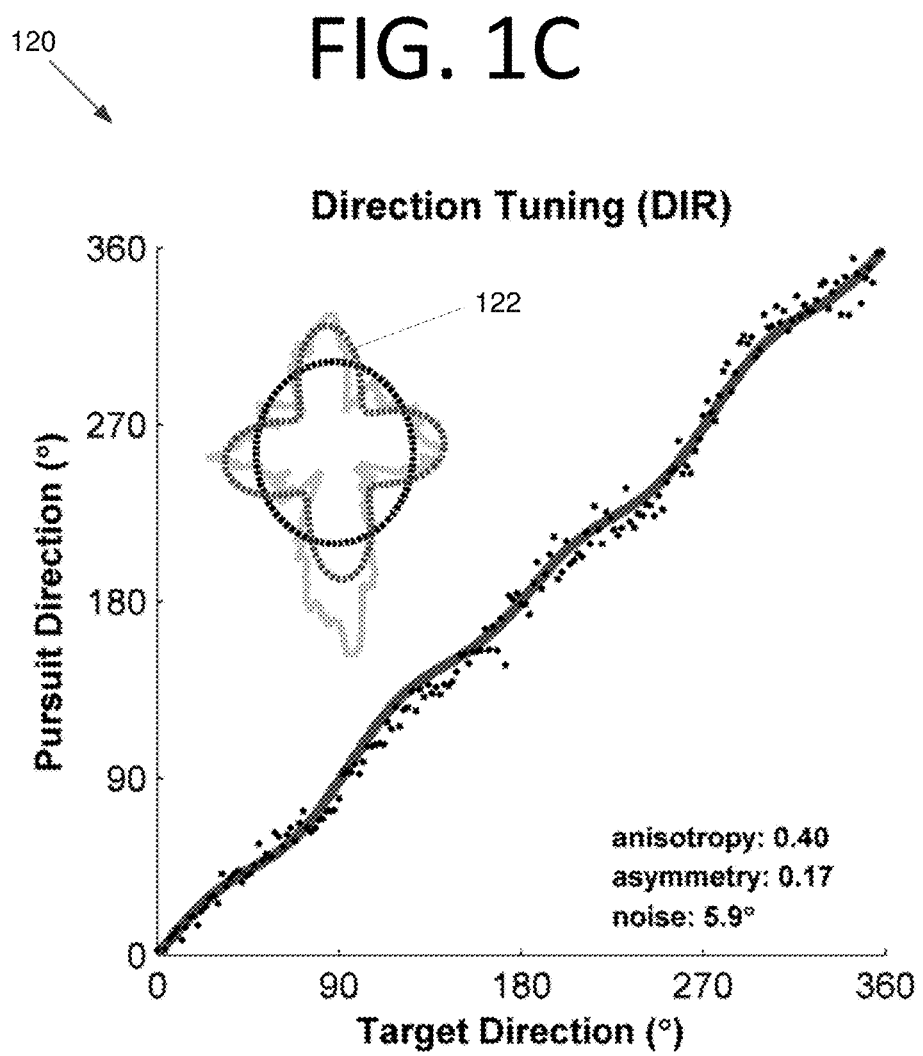

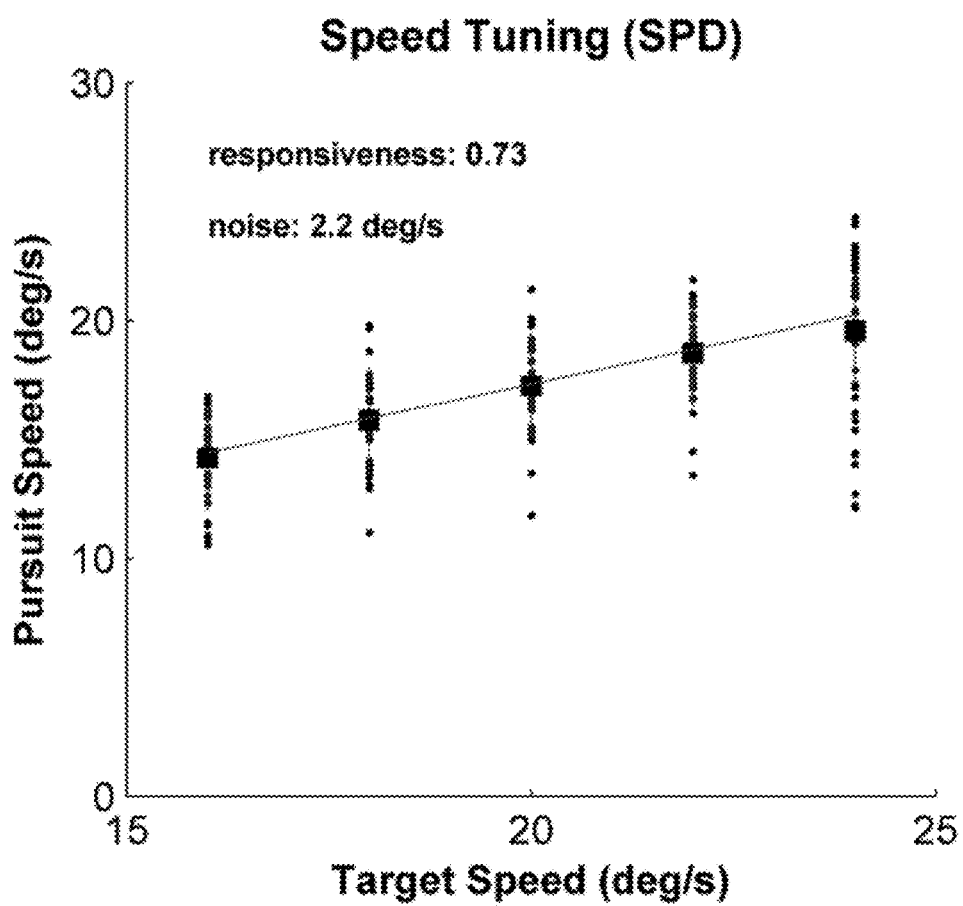

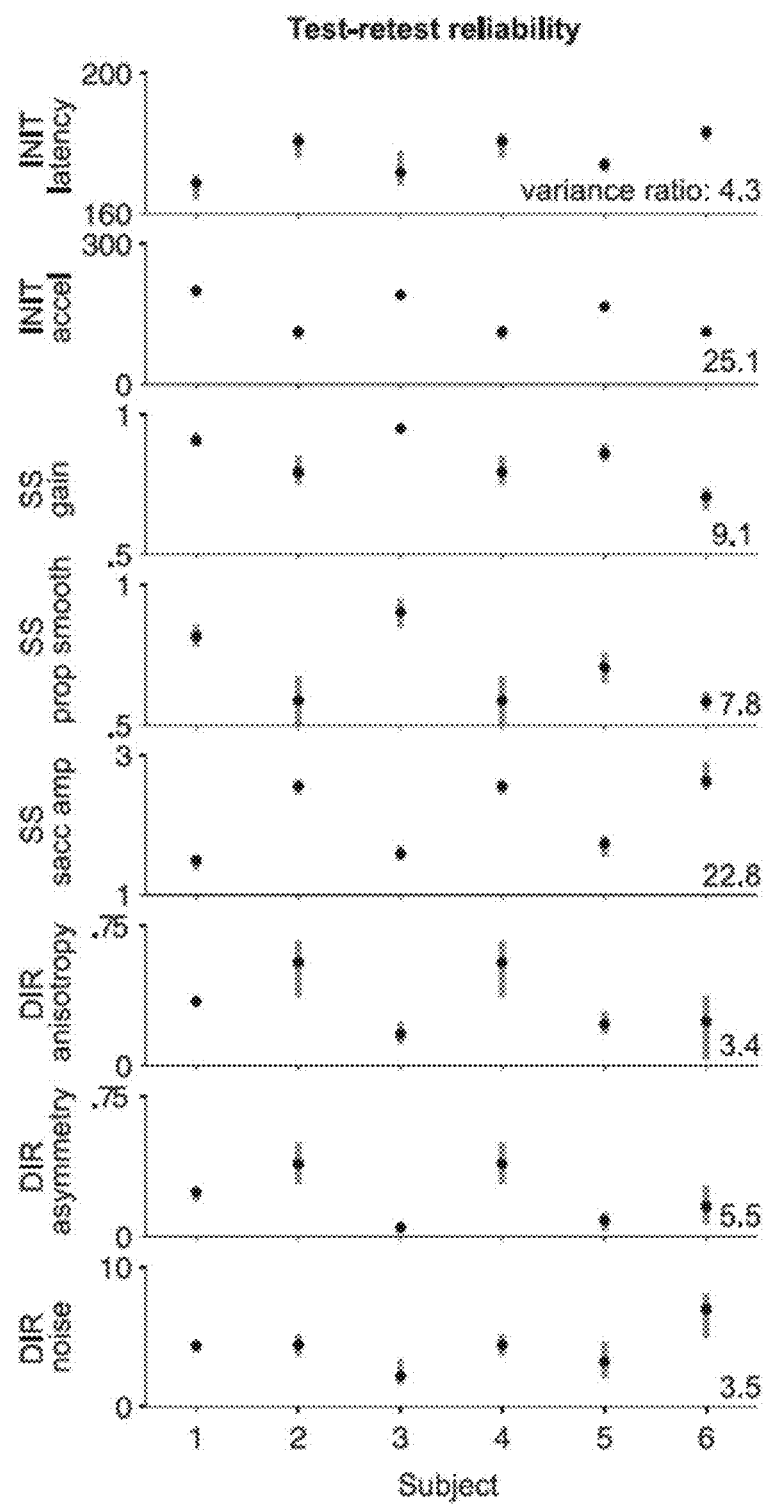

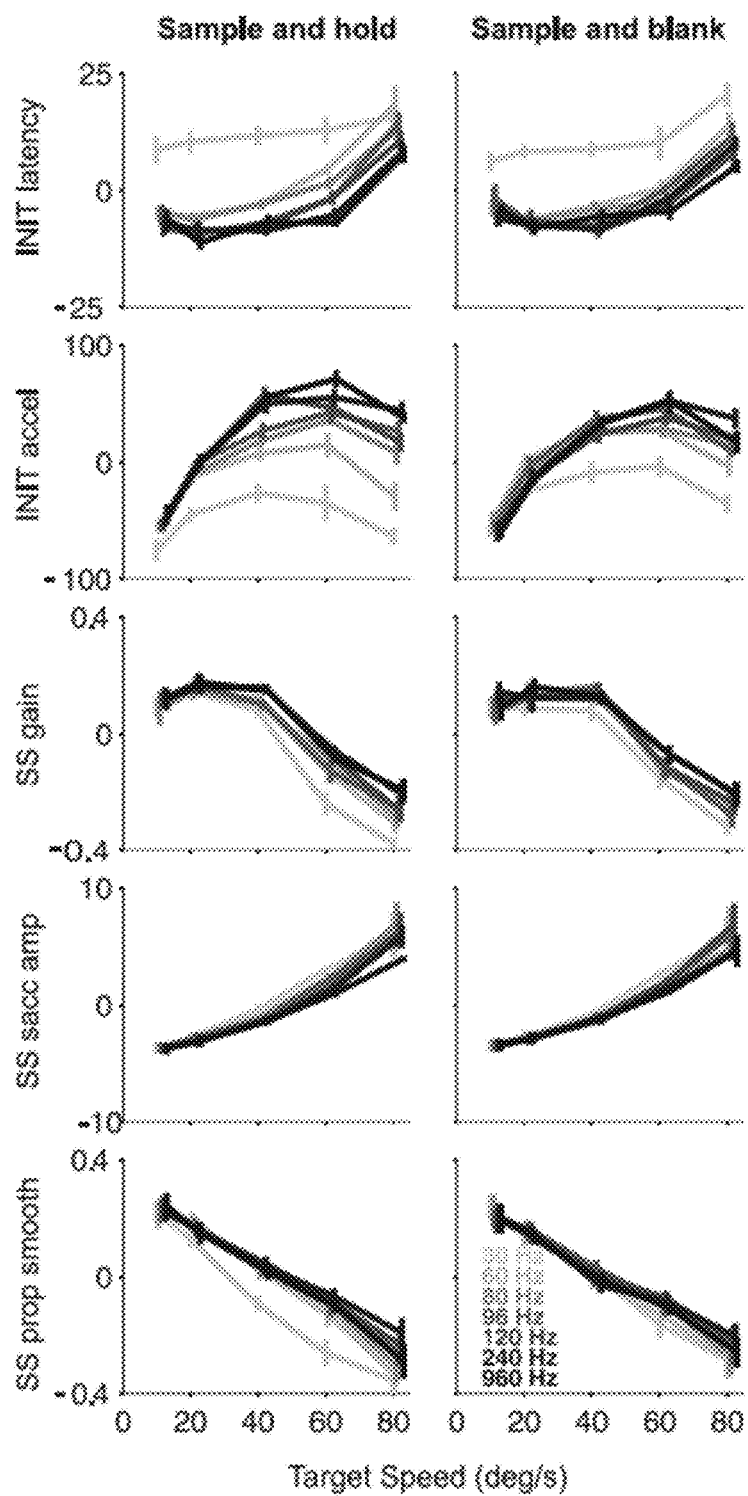

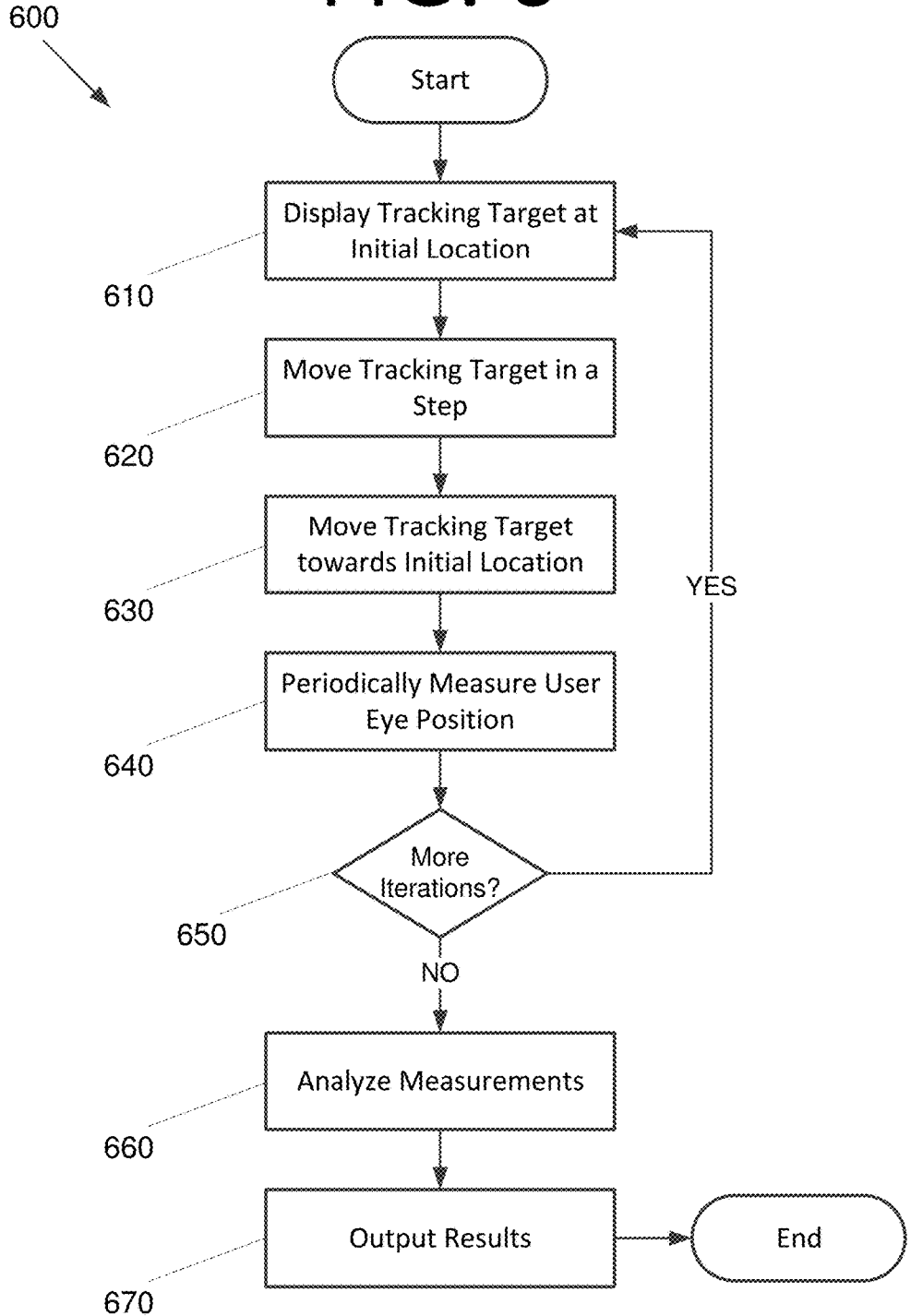

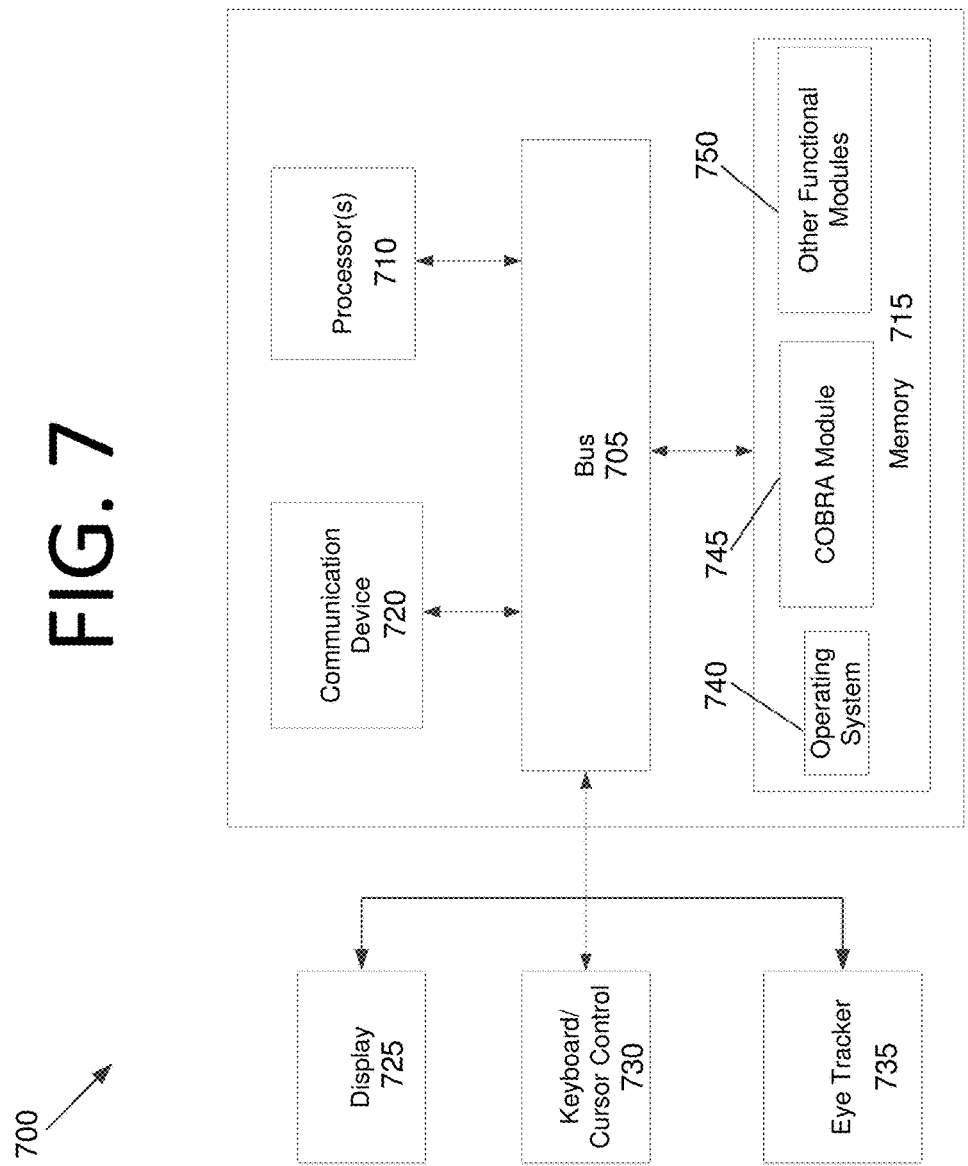

COMPREHENSIVE OCULOMOTOR BEHAVIORAL RESPONSE ASSESSMENT SYSTEM

CROSS REFERENCE TO RELATED APPLICATIONS

This application is a divisional of U.S. patent application Ser. No. 14/710,260, entitled "Comprehensive Oculomotor Behavioral Response Assessment," filed on May 12, 2015. U.S. patent application Ser. No. 14/710,260 claims the benefit of U.S. Provisional Application No. 61/994,673, entitled "Comprehensive Oculomotor Behavioral Response Assessment," filed on May 16, 2014. U.S. patent application Ser. No. 14/710,260 and U.S. Provisional Application No. 61/994,673 are hereby incorporated herein by reference in their entirety.

ORIGIN OF THE INVENTION

The invention described herein was made in the performance of work under a NASA contract by an employee of the San Jose State University Research Foundation and by an employee of the United States Government and is subject to the provisions of Public Law 96-517 (35 U.S.C. § 202) and may be manufactured and used by or for the Government for governmental purposes without the payment of any royalties thereon or therefore. In accordance with 35 U.S.C. § 202, the contractor elected not to retain title.

FIELD OF THE INVENTION

The present invention generally relates to visual assessment, and more particularly, to oculometric assessment of dynamic visual processing using eye tracking to assess a user's performance.

BACKGROUND OF THE INVENTION

Dynamic and peripheral visual processing remains more difficult to clinically assess than standard static foveal processing due at least in part to a lack of a standard, quantitative, reliable, and efficient screening technique and tool, as well as the lack of a codified set of performance standards. Impairment in dynamic visual processing and smooth-pursuit tracking can stem from myriad causes, including, but not limited to, stroke, lesions of the extrastriate visual cortex, cerebellar or brainstem damage, traumatic brain injury, autism, Alzheimer's disease, schizophrenia, degenerative retinal disease, pharmacological toxicity, aging, and spaceflight-induced visual impairment. Accordingly, a readily-available methodology and tool to assess dynamic visual processing may be clinically useful, and thus beneficial to patient populations.

SUMMARY

Certain embodiments of the present invention may provide solutions to the problems and needs in the art that have not yet been fully identified, appreciated, or solved by conventional clinical visual processing assessment technologies or other eye movement-based approaches. For example, some embodiments of the present invention pertain to an eye movement-based methodology and assessment tool that can quantify many aspects of human dynamic visual processing using a relatively simple and short (e.g., fifteen minutes or less) oculomotor task, noninvasive video-based eye tracking, and validated oculometric analysis techniques. The novel task of some embodiments is to track an unpredictably-presented sequence of radially organized step-ramp target trajectories that are designed to efficiently and systematically sample target location, direction, and speed and avoid anticipatory-motor responses. The method and system of such embodiments may use a high spatiotemporal precision and well-calibrated eye tracking methods. Optimized spatiotemporal filtering may be used for signal processing and saccade identification and removal, optimized movement-onset computation algorithms, and metric extraction algorithms, for example, in order to robustly compute a number of objective and reliable measures of the pursuit eye-movement response from a minimal number of trials.

In certain embodiments, ten quantitative oculometrics may be derived from the test and used for assessment. However, in other embodiments, more or fewer metrics may be used. Some embodiments include a novel vector projection-based method for computing a single impairment index from the full set or a subset of the metrics (i.e., the magnitude of impairment along a specific impairment direction in the multi-dimensional space of the oculometrics). Together, the set of metrics provides a multi-dimensional quantitative assessment of dynamic visual processing, which may degrade under several disease conditions and/or brain insults including, but not limited to, degenerative retinal disease (e.g., retinitis pigmentosa, macular degeneration, etc.), elevated intracranial pressure, glaucoma, brain injury (e.g., impact trauma, blast trauma, stroke, aneurysm, etc.), drug intoxication (e.g., alcohol, barbiturates, nefadozone, etc.) drug toxicity (e.g., tetracycline antibiotics, etc.), chemical exposure (e.g., industrial chemicals, insecticides, nerve agents, etc.), degenerative disease (e.g., multiple sclerosis, Parkinson's disease, Alzheimer's disease, cerebellar atrophy, etc.), neurodevelopmental disorders (e.g., autism spectrum), psychiatric illness (e.g., biopolar disorder, schizophrenia, depression, etc.), fatigue, stress, and other conditions.

By examining the eye movement responses to a modified Rashbass step-ramp pursuit-tracking task, for example, distinct performance measurements may be generated that are associated with pursuit initiation (e.g., latency and open-loop pursuit acceleration), steady-state tracking (e.g., gain, catch-up saccade amplitude, and the proportion of the steady-state response consisting of smooth movement), direction tuning (e.g., oblique effect amplitude, horizontal-vertical asymmetry, and direction noise), and speed tuning (e.g., speed responsiveness and noise). The metrics for pursuit initiation may be standard measures that quantify the promptness and vigor of movement onset. The steady-state tracking metrics may include standard measures of pursuit gain, catch-up saccade amplitude, and the proportion of eye displacement consisting of smooth tracking. Sets of direction-tuning and speed-tuning metrics may be converted directly to psychometric thresholds without the need to perform a time-consuming motion discrimination psychophysical task. Stated differently, while prior eye movement-based approaches are qualitative in nature, some embodiments of the present invention employ a more systematic and quantitative approach, both in the behavioral task and in the analysis method, yielding a final data set that can be interpreted by one without a high degree of sophistication in the field of oculometrics.

In an embodiment, a computer-implemented method includes displaying a tracking target, by a computing system, at an initial location on a display for a randomized delay interval. After the randomized delay interval has elapsed, the computer-implemented method also includes moving the tracking target in a step, by the computing system, to a random location on the display, moving the tracking target on the display, by the computing system, towards the initial location at least until the tracking target crosses the initial location, periodically measuring, by the computing system, user eye position while the user is following the tracking target, and repeating the moving of the tracking target and eye position measurement, by the computing system, a plurality of times. The computer-implemented method further includes analyzing the user eye response measurements, by the computing system, to determine a plurality of quantitative performance measures and outputting, by the computing system, results of the analysis.

In another embodiment, a system includes a computing system including a display. The computing system is configured to display a tracking target on the display. The computing system also includes an eye tracker configured to take periodic measurements of eye position of a user based on the displayed tracking target position. The computing system is further configured to receive the periodic measurements from the eye tracker, analyze the received periodic measurements to determine a plurality of quantitative performance measurements and display the eye position measurements and/or results of the analysis, or transmit the received periodic measurements to another computing system that analyzes the received periodic measurements to determine the plurality of quantitative performance measurements.

In yet another embodiment, a computer program is embodied on a non-transitory computer-readable medium. The program is configured to cause at least one processor to receive a plurality of eye position measurements tracking a user's following of a tracking target over time. The computer program is also configured to cause the at least one processor to analyze the plurality of eye position measurements to determine a plurality of quantitative metrics, or transmit the plurality of eye position measurements to a remote computing system to analyze the plurality of eye position measurements and determine the plurality of quantitative metrics. Based on the plurality of quantitative metrics, the computer program is further configured to cause the at least one processor to provide an indication of whether the user has a brain injury, whether the user has a disease, whether the user is faking an injury, whether the user is intoxicated, or any combination thereof.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which:

FIG. 1A illustrates histograms of latency and acceleration for pursuit initiation, according to an embodiment of the present invention;

FIG. 1B illustrates histograms of pursuit gain, average amplitude of saccadic intrusions, and the proportion of eye displacement that consisted of smooth tracking for steady-state tracking, according to an embodiment of the present invention;

FIG. 1C is a direction-tuning (DIR) scatterplot illustrating pursuit direction as a function of target direction for each trial, according to an embodiment of the present invention;

FIG. 1D is a scatterplot illustrating speed tuning, according to an embodiment of the present invention;

FIG. 2 illustrates graphs of test-retest reliability, according to an embodiment of the present invention;

FIG. 3 illustrates graphs of validation and oculometric measures with sampled motion stimuli, according to an embodiment of the present invention;

FIG. 6 is a flowchart illustrating a process for quantitatively analyzing visual performance, according to an embodiment of the present invention; and FIG. 7 is a block diagram of a computing system configured to perform oculometric assessment, according to an embodiment of the present invention.

DETAILED DESCRIPTION OF THE EMBODIMENTS

Figure 4:
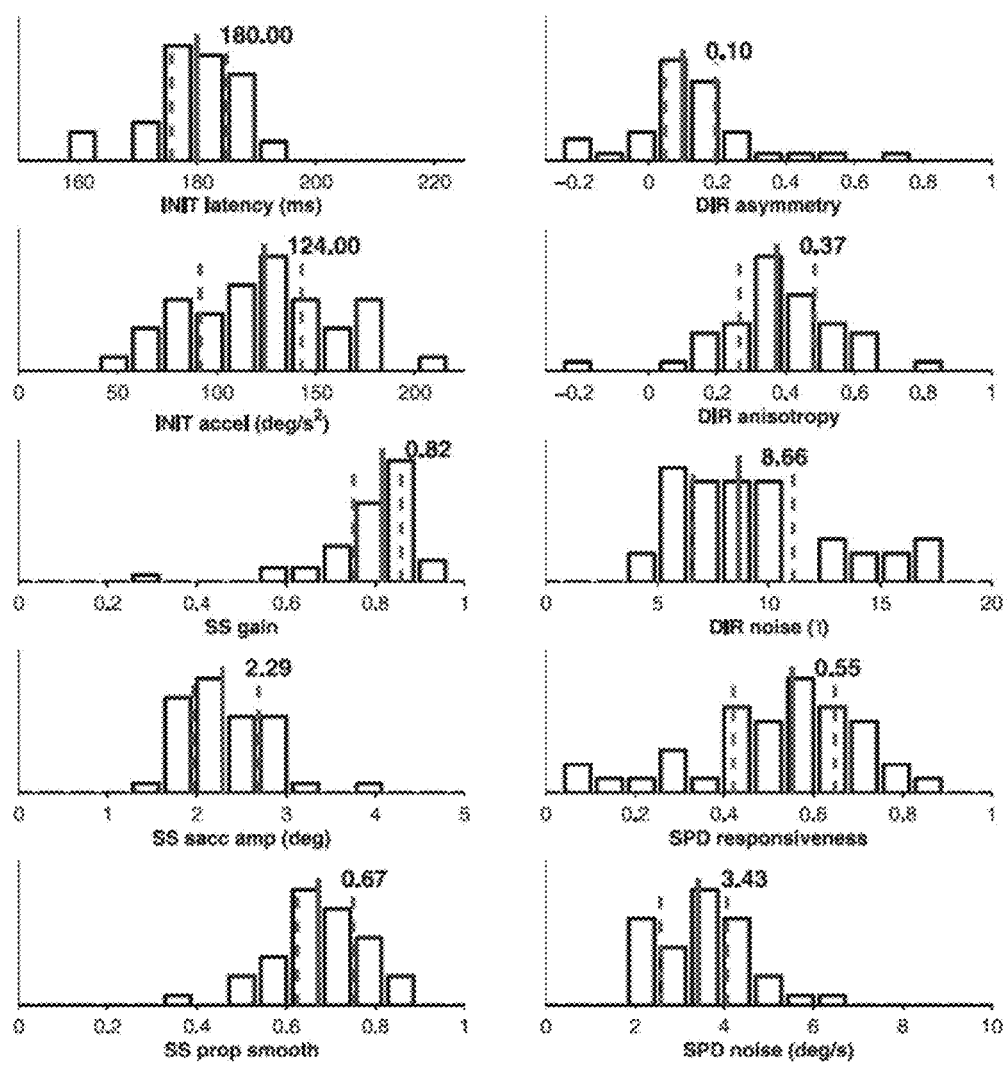
FIG. 4 illustrates graphs of the population distribution set of 10 metrics for 41 normal subjects, according to an embodiment of the present invention.

Some embodiments of the present invention pertain to an eye movement-based methodology and assessment tool that can quantify many aspects of human dynamic visual processing using a relatively simple and short oculomotor task, noninvasive video-based eye tracking, and validated oculometric analysis techniques. Using eye movement tracking presents a significant advantage over conventional assessment techniques. If standard psychophysical measures of perception and brain function are used, these studies take approximately an hour just to measure one variable, and it can take many days to measure multiple variables. Using the rapid and precise measurements afforded by eye tracking, the efficient behavioral task, and the eye movement data processing and analysis of some embodiments provides a dramatic increase in efficiency, sensitivity, and reliability over traditional psychophysics-based approaches and other conventional eye movement-based approaches.

Another significant advantage of some embodiments is providing a quantitative assessment rather than a qualitative assessment. For over 100 years, it has been understood that many brain abnormalities may alter eye movements. See A. R. Diefendorf and R. Dodge, "An Experimental Study of the Ocular Reactions of the Insane from Photographic Records," Brain, 31(3), pp. 451-489 (1908). However, conventional tests merely require a person to follow a finger, similar to what a police officer does when issuing a field sobriety test. There is no detection metric per se, other than the qualitative percept of "normal eye movements" by the officer giving the test. However, the application of an efficient testing paradigm that allows rapid quantitative assessment in some embodiments both improves speed and offers consistency of analysis, which may be useful to assess intoxication due to alcohol, other drugs, or a combination thereof.

In some embodiments, peripheral vision, prediction, and other factors may be measured to determine both the type and degree of brain injury or impairment. For instance, such a test may be used to determine whether a football player who is not showing obvious symptoms has a concussion. In another instance, such a test may be used to determine whether a soldier exposed to a blast who is also not showing obvious symptoms has suffered a mild traumatic brain injury. Precursors to actual, irreversible brain damage, swelling, and other structural damage may be identified before it is too late to circumvent or mitigate damage. Furthermore, certain embodiments may be used to identify enhanced sensory motor capabilities that are present in superior pilots, athletes, etc. Additionally, the Departments of Motor Vehicles in various states may use the test to objectively determine whether an individual is fit to drive. Furthermore, individuals with degenerative diseases, brain injuries, or who have experienced other types of brain insults may use the results of the test in collaboration with medical care providers to inform day-to-day decisions about whether an individual is fit to drive or perform other dangerous activities.

Some embodiments may cost $1,000.00 or less, and require no medical training to use, making them affordable and usable by individuals and various entities (such as high schools) that may not have significant financial resources to devote to more expensive medical technologies or the expertise required for their operation. In the high school scenario, coaches, trainers, parents, or any other individual without extensive training in oculometrics may administer a test on the sideline to assess functional brain health. If a player demonstrates an impairment and thus fails the test, in order to prevent exacerbation of the injury and/or permanent damage, the player may be prevented from playing again until the player passes a subsequently administered test.

Furthermore, the COBRA system of some embodiments may identify whether an injury is being faked. The use of a baseline in some embodiments helps to prevent test takers from "throwing the test." A person who tries to fake such an injury will likely appear far worse than the worst measurement for any real injury. For instance, the eye movement traces will appear unrealistically unresponsive to the stimulus motion, and the test taker's own eye movements involuntarily give up the lie. In other words, it is not possible to generate well-behaved, yet subtly diminished, performance of tracking eye movements without failing to perform the task, which would be detected as non-compliance as opposed to neural impairment.

Additionally, some embodiments not only measure whether an individual is better or worse than a baseline, but further provide an indication of whether the individual is improving or deteriorating or altered from his or her own baseline. As such, each individual has his or her own "fingerprint" that is unique to the individual. For instance, see cloverleaf graph 100 of FIG. 1A.

Cloverleaf 122 in DIR scatterplot 120 of FIG. 1C is measure of a person's own idiosyncratic oblique effect. Each individual has a differently shaped cloverleaf that is unique to that specific individual. The cloverleaf will look the same unless the person is injured, impaired, or deteriorating in some way.

Different injuries and diseases cause recognizable patterns, and the type of injury or disease may be diagnosed from the pattern. For example, degenerative retinal conditions are characterized by sluggish initiation metrics (e.g., long latencies, low accelerations, etc.) caused by impaired peripheral image motion processing at the level of the retina. On the other hand, normal steady-state metrics (i.e., normal gain, normal saccade amplitude, etc.) as the steady-state portions of tracking are driven by perceived object motion, which is unimpaired during foveally-driven processing. For instance, an asymmetry between performance for one eye with respect to the other eye may indicate that one side of the brain has been damaged by a stroke, a tumor, or another malady, or that the extraocular muscles of one eye have been damaged. Also, for certain injuries and diseases, improvement or deterioration of a patient over time may be measured.

Certain embodiments may be used regularly during routine medical exams or a standard optometry test. These tests may indicate that a person has a condition that he or she is not aware of, such as early-stage retinitis pigmentosa or glaucoma. By the time impairment manifests itself in reading a typical eye chart, or by the time that the visual deficit is so severe that it becomes perceptually apparent to the patient, irreversible, and potentially preventable, damage may already have occurred. In this manner, the tests described herein may be the eye equivalent of an electrocardiogram (EKG) that preemptively identifies treatable cardiac problems before they progress to a heart attack.

Rashbass-Like Task

For the tasks of some embodiments, specially tailored variants of the classic Rashbass step-ramp paradigm are used. See C. Rashbass, "The Relationship between Saccadic and Smooth Tracking Eye Movements," Journal of Physiology, No. 159, pp. 326-338 (1961). In an embodiment, subjects began each trial fixating the target (a small red spot in this embodiment) in a primary position and pressing a mouse button when they chose. As such, this was a self-paced test. Subjects then fixated the red spot for a randomized duration drawn from a truncated exponential distribution for a mean time of 700 ms, with a minimum of 200 ms and a maximum of 5000 ms to defeat possible response strategies based on temporal anticipation of motion onset. The series of experiments that were conducted are discussed below.

After the randomized delay interval had elapsed, the tracking target made a small step in a particular direction, and immediately began moving back toward the initial fixation location. The step size was set such that the target crossed its original fixation location 200 ms after motion onset, therefore reducing the likelihood of an initial catch-up saccade. In all experiments of this embodiment, each session consisted of a total of only 180 trials to maintain a high level of alertness and to complete the test in a clinically reasonable amount of time (15 minutes). The distributions of possible directions and speeds differed across the three experiments presented here, so additional experiment-specific details are given below.

Eye-Movement Recording

In this experiment, eye position was sampled at 240 Hz with an ISCAN™ video-based eye tracker. The eye position traces were calibrated with a six parameter fit to the raw digital values for fixations at nine screen locations within a Cartesian grid. This yielded an average precision of 0.32° (i.e., the standard deviation of eye position while fixating across the 41 subject population), which provides an upper limit on the tracker noise that may have perturbed the measured values of the metrics.

However, the shared variance across subjects between the ten metrics and the eye tracker precision was 4% on average, with the two noise metrics showing the highest proportion of shared variance, as expected (direction noise: 14%, speed noise: 7%). Thus, tracker noise only weakly impacted the results. Saccades were detected and deleted from the raw eye-movement data using a nonlinear median filter to remove the low-frequency components in the eye-velocity trace due to smooth tracking, then taking the correlation between a saccade-shaped velocity template and the resulting trace to find and remove saccadic movements of 0.2° or larger.

Reliability Experiment

The first experiment measured across-session variability for all metrics except the two speed-tuning metrics for six subjects. Each session consisted of 180 tracking trials of the Rashbass step-ramp stimulus, corresponding to 180 directions sampled without replacement from 0° to 358° (in 2° increments) at a fixed speed of 20 deg/s. Stimuli were displayed on an Eizo FlexScan™ T966 60 Hz CRT monitor with a resolution of 1024×768. At the viewing distance of 470 mm, pixels were 0.04×0.04 deg). Each subject completed five repetitions of the 15 minute task over a period of less than three weeks, with the exception of one observer who completed only four repetitions.

Validation Experiment

The second experiment tested whether the set of metrics of this embodiment could detect degradations of stimulus motion due to coarse spatiotemporal sampling of the motion trajectory. This experiment highlights another potential use of the methodology—assessing variability across stimulus conditions due to differences in display fidelity, as opposed to assessing variability across sessions or observers due to differences in human performance. In this experiment, the sensitivity of the oculomotor system was used to assay the perceived quality of a sampled motion stimulus.

To provide well-controlled sampled motion, a laser galvanometer system was used that back-projected a spot on a translucent screen with its trajectory sampled at one of seven temporal frequencies (30, 60, 80, 96, 120, 240, and 960 Hz) in one of two sampling conditions. The sample-and-hold condition simulated the sampling properties of a liquid crystal display (LCD), with the laser spot illuminated continuously as it stepped through the trajectory. The sample-and-blank condition simulated the sampling properties of a cathode ray tube (CRT) display, with the laser spot illuminated for only the first half of each sample. The intensity of the laser spot was adjusted to match the temporal average luminance in both sampling conditions.

This experiment used a standard Rashbass step-ramp stimulus moving horizontally to either the left or the right at one of five possible speeds (10, 20, 40, 60, and 80 deg/s), drawn randomly on each trial. Six subjects (five naive) ran four to five experimental sessions consisting of two 180 trial blocks, one block for each sampling condition. For each subject, the data was collapsed across all sessions for each sampling condition, then the five metrics quantifying the vigor of pursuit initiation (latency and acceleration) and the quality of steady-state tracking (gain, saccade amplitude, and proportion smooth) were computed.

The stimuli used in the sampled motion experiment did not vary in direction (other than randomly left or right). Thus, the validity of the three direction-tuning metrics was not examined in this experiment. For each subject, the data was normalized by subtracting out the mean value to isolate the performance changes resulting from the stimulus differences. This allowed averaging across subjects while minimizing the variability caused by stimulus-independent inter-subject differences in overall performance.

Population Baseline Experiment

The third experiment catalogued the full set of metrics for a baseline population of 41 subjects (19 female, age range 20-56 years, median 27, 35 of the 41 subjects had little or no prior experience as subjects in smooth-pursuit experiments). This experiment was designed to provide subjects with no prior information about the timing of motion onset, the motion, or the speed of motion to ensure that the oculomotor behavior was driven as much as possible by the visual stimulus properties of the moving target rather than by cognitive expectations. On each trial, the target speed was randomly either 16, 18, 20, 22, or 24 deg/s. Target direction was randomly sampled without replacement from a uniform distribution from 0° to 358° in 2° increments. Stimuli were displayed on the Eizo FlexScan T966 as in the reliability study above. A scripted set of instructions was provided to each subject, given below:

"You will be performing a tracking task that will last for approximately fifteen minutes, consisting of 180 trials. At the beginning of each trial, you will see a small red spot appear in the center of the screen. When you are rigidly fixating the central spot, click the mouse to indicate that you're ready. After a randomized duration, the spot will make a small step away from the central fixation location in a randomized direction and will begin moving toward the original fixation location and then off toward the edge of the monitor. Track the motion of the red spot as best you can as long as it is visible."

Subject age and measured visual acuity were also recorded using the Freiburg Visual Acuity™ software package.

Measurements of Pursuit Initiation (Init)

An automated "hinge" model was used to mark the onset of the pursuit movement. Because the tracking target moved in a fixed random direction, to increase the signal-to-noise ratio, velocity was used along the direction of target motion to measure pursuit onset by taking the dot product of the horizontal and vertical velocity traces and the direction of target motion. The hinge consists of two line segments, baseline and response, each 100 ms in duration, occurring consecutively. Pursuit latency was defined as the point at which the two line segments intersected that minimized the root mean square (RMS) error with the observed data. Three constraints were added to the fitting algorithm to increase its robustness. The baseline velocity was forced to be zero, the response acceleration was constrained to be positive, the latency was constrained to be between 100 and 400 ms, and the error function was weighted by a "recinormal" prior-probability distribution of latencies on a similar task using $M=5.4$ s$^{-1}$ and $SD=2$ s$^{1}$, where M is the mean and SD is the standard deviation, based on an expected value of 185 ms. The algorithm minimized the weighted-error between the best fitting two-parameter hinge model to the velocity trace to yield the "pursuit latency" and the initial "pursuit acceleration" metric that characterizes the open-loop pursuit response.

Measurements of Steady-State Tracking (Ss)

For the three steady-state tracking metrics, the steady-state interval was defined from 400 to 700 ms following target motion onset to allow enough time for eye velocity to reach a steady-state value, while ensuring that the stimulus motion was still present on all trials. The "steady-state gain" metric was defined as the ratio of eye velocity along the stimulus direction to target velocity. The average catch-up saccades amplitude was calculated for each trial and the "saccade amplitude" metric was defined as the median across trials. The "proportion of smooth pursuit" metric was defined as the ratio of eye displacement during smooth pursuit to total eye displacement.

Direction-Tuning Measurements (Dir)

The direction of the pursuit response during the steady-state interval was measured to quantify the direction-tuning properties of the pursuit response. Direction gain was defined as the local slope of the function relating pursuit direction to stimulus direction, which shows deviations from unity slope (i.e., a wiggly line in Cartesian coordinates) that peaks near the cardinal and oblique axes, consistent with an expansion of direction space around the cardinal axes and a contraction around the oblique axes. In polar coordinates, this anisotropy in direction gain takes on a cloverleaf shape, with leaves protruding past unity gain near the cardinal axes and local regions of less-than-unity gain near the oblique directions. To describe the shape of the cloverleaf anisotropy, the direction-tuning curves were fit with a three-parameter function, ignoring points with directional errors greater than 30°. The first parameter $\alpha$ describes the magnitude of the cardinal-oblique anisotropy, the second parameter $\beta$ describes the asymmetry between the size of the vertical and horizontal lobes, and the third parameter $\Delta$ describes the orientation of the cloverleaf. The fitting function is given by:

$$f(\varphi)=1+\alpha\cdot\cos(4(\varphi+\Delta))-\beta\cdot\cos(2(\varphi+\Delta)) \quad (1)$$

the best-fitting, local linear-regression slope was measured in 1° increments within a 30° window centered on a particular direction. The resulting plot of slope versus direction was fit with Eq. (1) to compute the direction anisotropy and direction asymmetry metrics. The difference was taken in the direction of the pursuit response across pairs of neighboring stimulus directions and pooled across all directions to yield a distribution of difference measures based on the observation that directional noise is isotropic. "Directional noise" is defined as the standard deviation of the distribution of difference measures.

Speed-Tuning Measurements (Spd)

To quantify the signal-to-noise properties of speed processing, the mean speed of the pursuit response was measured along the direction of target motion during the steady-state interval for each target speed. The speed responsiveness metric was computed as the slope of the linear regression of the mean eye speed measures across target speeds. The speed-noise metric was then computed as the mean standard deviation in eye speed, averaged across target speeds.

Results

The summary metrics for one subject from one 15 minute session are shown in FIGS. 1A-D, grouped by the measurement types (INIT, SS, DIR, SPD). Each 15 minute session consisted of 180 trials and yielded 10 metrics. Histograms 100, 110 in FIGS. 1A and 1B plot across-trial measurements of pursuit motor function. The oculometric direction-tuning and speed-tuning measurements are shown in graphs 120, 130 of FIGS. 1C and 1D. The measurements of INIT yield a skewed recinormal distribution of latencies 102 and a quasinormal distribution of accelerations 104. See FIG. 1A. Measurements of SS tracking (400-700 ms after motion onset) include pursuit gain 112, the average amplitude of saccadic intrusions 114, and the proportion of eye displacement that consisted of smooth tracking 116. See FIG. 1B. DIR scatterplot 120 of FIG. 1C shows pursuit direction as a function of target direction for each trial, and cloverleaf 122 shows cloverleaf anisotropy (dashed cloverleaf) referenced to a circle of unity gain. SPD scatterplot 130 of FIG. 1D plots pursuit speed as a function of target speed (solid black circles), the across-trial median (solid black square), and the speed-tuning slope (solid line).

For this subject, the median latency of pursuit initiation was 162 ms with a median acceleration of 182 deg/s$^2$. The median gain during the steady-state interval was 0.87, the median amplitude of the average catch-up saccade was 1.66°, and the proportion of eye displacement that can be attributed to smooth movement was 0.78. The direction-tuning of the pursuit response is summarized by two parameters (see Eq. (1)). The anisotropy (oblique effect) of 0.40 and the asymmetry (horizontal-vertical bias) of 0.17 together capture the overall cloverleaf shape (see cloverleaf 122 in FIG. 1C) of the pursuit direction-gain function. The direction noise is captured by the mean standard deviation in eye speed of 5.98 in the pursuit response. For this subject, the signal-to-noise properties of the speed-tuning are summarized by a speed responsiveness of 0.73, the slope of the quasi-linear speed-response function, and by the speed noise of 2.2 deg/s. Whereas the initiation and steady-state tracking metrics represent median measurements made from individual trials, the direction and speed-tuning metrics are derived from pursuit behavior across the entire set of trials.

Reliability

To assess the test-retest reliability of the metrics, six subjects were run in an experiment that quantified all metrics, except for the two speed-tuning metrics. The objective of this test was to compare the intrasubject variability across repeated sessions to the intersubject variability. Each filled circle in graphs 200 of FIG. 2 plots the average across five repeated measurements for one subject. Gray error bars illustrate the entire range of the measurements for that observer. All eight metrics that were tested showed significant differences across subjects (p<0.0001), and the ratio of average intersubject variance across subjects for a given metric to the average intrasubject variance across sessions for a given subject ranged from 2.6 to 14.8. In many cases, the across-subject measurements are completely non-overlapping. These results indicate that the metrics provide sufficient test-retest reliability to quantify consistent performance differences across individuals, despite the fact that potential sources of within-subject variability were not controlled, e.g., systematic circadian-rhythm variations or random effects such as meal timing or fatigue.

Validity

To assess the ability of the metrics to detect degradations in the visual stimulus (i.e., that the metrics are valid measures of dynamic visual information processing), six subjects were run in an experiment using sampled motion, which is known to produce both degraded motion perception and smooth-pursuit tracking. A classic Rashbass tracking task was used with only horizontal (randomly left or right) motion, and the five INIT and SS metrics were measured. The results on the reliability experiment demonstrated large across-subject variability, which tends to reduce the power to detect possible effects of sampling rate. To minimize the impact of that variability, for each subject, the data was first normalized by subtracting out the mean value across all target speed and sampling rate conditions.

Degraded visual motion in sampled stimuli strongly impairs pursuit initiation, whereas steady-state tracking shows more subdued effects as expected under closed-loop control. Validation of oculometric measures with sampled motion stimuli are shown in graphs 300 of FIG. 3. Each row contains axes plotting one oculometric measurement as a function of target speed: one set of axes in the sample-and-hold condition (left-hand column), and one set of axes for the sample-and-blank condition (right-hand column). The shade series in each set of axes represents the sampling frequencies from 30 Hz (light gray) to 960 Hz (black). The data in each graph is zeroed about the mean value across all target speeds and sampling frequencies for each observer. Error bars plot the standard error of the mean across observers.

Using a three-way Analysis of Variance (ANOVA), clear main effects of sampling rate were observed on both initiation metrics (latency: $F(6,5)=96.0$, acceleration: $F(6,5)=41.5$, both ps<0.0001), as well as a significant interaction between sampling rate and speed (latency: $F(24,314)=2.7$, acceleration: $F(24,314)=6.9$, both ps<0.0001). Significant but more subdued main effects of sampling rate on all three steady-state tracking metrics were also observed (gain: $F(6,5)=15.9$, $p<0.0001$, saccade amplitude: $F(6,5)=3.2$, $p<0.05$, proportion smooth $F(6,5)=9.7$, $p<0.0001$), as well as significant interaction between sampling rate and speed (gain: $F(24,314)=1.9$, $p<0.01$, saccade amplitude: $F(24,314)=1.9$, $p<0.01$, proportion smooth $F(24,314)=4.32$, $p<0.0001$). Whereas the significant main effects demonstrate that these five oculometric measures are sensitive to the quality of sampled motion, the significant interactions show that sampling rate has a larger impact at higher speed consistent with frequency-domain predictions.

Baseline Population Metrics

Graphs 400 of FIG. 4 show the population distribution of a set of 10 metrics for 41 normal subjects, nearly all of whom were naive to previous oculomotor or psychophysical testing. The subjects ranged in age from 20 to 56 years (median of 27) and they had static visual acuity that ranged from −0.29 to 0.44 log MAR (median −0.20). log MAR is a base-10 logarithmic version of the standard Snellen visual acuity, which expresses the distance at which an observer can discern a set of letters or symbols compared to the distance at which those symbols can be discriminated with "standard vision." For example, 20/20 becomes 0 (i.e., $\log_{10}(20/20)=0$), 20/15 becomes −0.125 (i.e., $\log_{10}(20/15)=-0.125$), 20/40 becomes 0.3 (i.e., $\log_{10}(20/40)=0.3$), and 200/20 becomes 1 (i.e., $\log_{10}(20/200)=1$). With high direction and speed uncertainty in the motion of the step-ramp stimulus, the median pursuit latency was 180 ms, with a median initial pursuit acceleration of 124 deg/s². The median steady-state pursuit gain was 0.82, with a median proportion smooth of 0.67 and median catch-up saccade amplitude 2.3 deg. The median direction noise was 8.66° with a median cardinal-oblique anisotropy of 0.37 and a median vertical-horizontal asymmetry of 0.10. This data can be converted into a direction-tuning threshold of 6.3° along the cardinal axes and 13.7° along the oblique axes. The median speed responsiveness was 0.55 with median speed noise of 3.4 deg/s. This data can be converted into a median speed-discrimination threshold of 6.23 deg/s or a Weber fraction of 31%.

Figure 5:
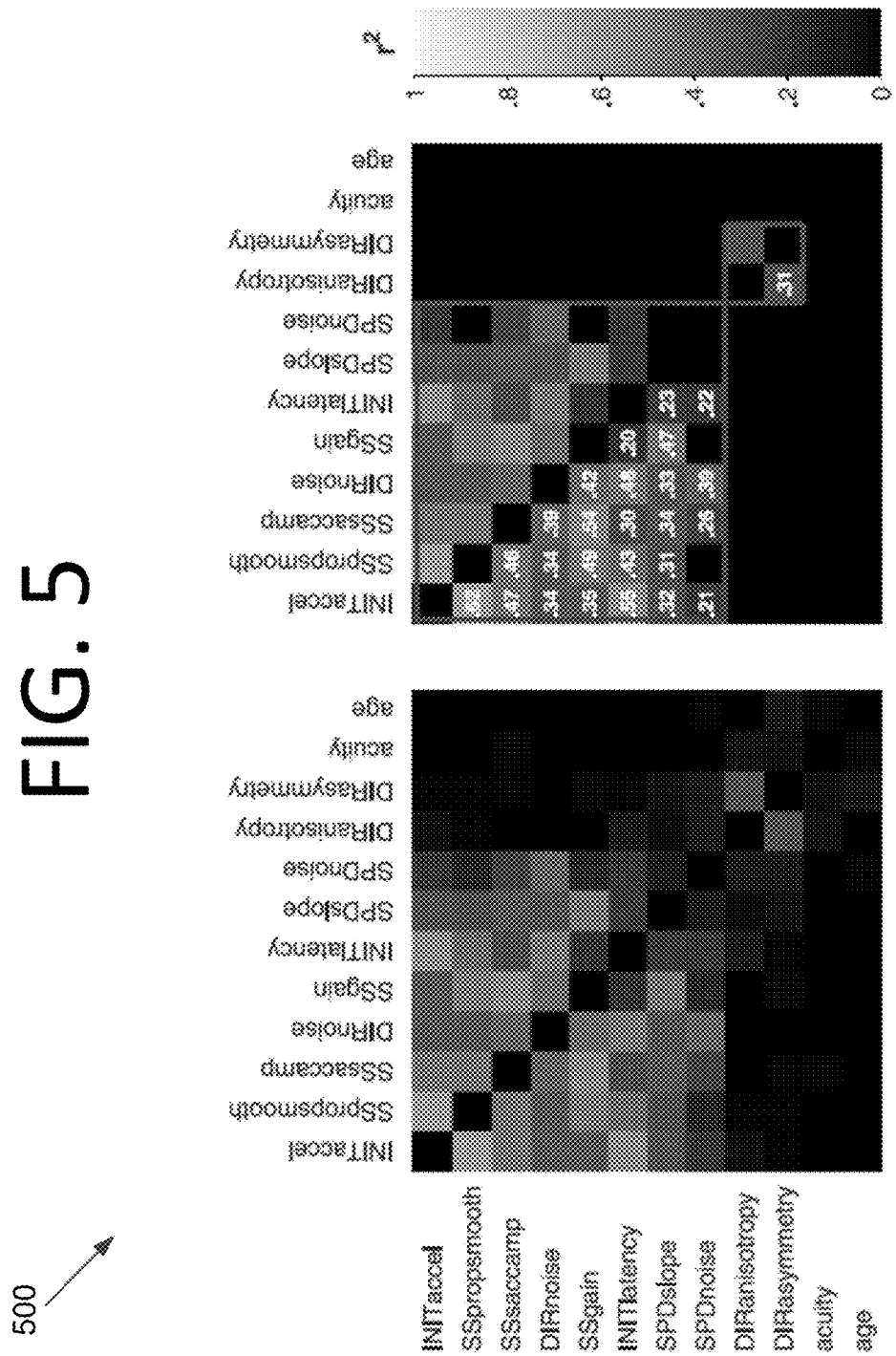
FIG. 5 illustrates graphs plotting correlation matrices for the sets of metrics, according to an embodiment of the present invention.

To quantify the extent to which the various metrics provide independent information, the degree of correlation was measured between the metrics across the population of 41 subjects. Graphs 500 of FIG. 5 plot correlation matrices between the sets of measurements, illustrating the range of $r^2$ values from 0.0 to 0.62. The sets of initiation and speed metrics share a significant proportion of underlying variance, but on average, only about a quarter of the variance (mean 23%) is shared between any pair of two metrics. The two metrics quantifying the pursuit oblique effect anisotropy were somewhat correlated with one another ($r^2=0.31$), but uncorrelated with the set of eight other metrics (mean $r^2=0.03$, $p>0.05$). Lastly, all 10 oculometrics were uncorrelated with both static visual acuity (Pearson's R, $p>0.05$, $r^2<0.06$) and age (Pearson's R, $p>0.05$, $r^2<0.08$). To highlight this clustering evident in the correlation matrix, "families" of metrics were grouped whose mutual correlation was Pearson's R, $r^2>0.2$ (solid boundaries on right graph). In some embodiments, subsets of metrics similar to these "families" are used to derive detection metrics for specific maladies.

Oculometric Measures

Some embodiments use 10 oculometrics measured with a 15 minute radial motion-tracking task, although more or fewer metrics may be used in certain embodiments. Five of the metrics are standard measures of vigor of the smooth-pursuit response and five quantify sensitivity to stimulus direction and speed. First, the test-retest reliability of eight of the metrics was assessed. The measurements were observed to be remarkably stable across sessions, showing significantly less variability as compared to the variability across subjects. Second, when tracking degraded motion stimuli, significant decrements were observed in both initiation metrics, as well as the three steady-state tracking metrics, validating the ability of the metrics to detect degradation of visual motion processing. Last, the full set of metrics was measured for a population of 41 normal (mostly naive) subjects. This provides a much more extensive baseline dataset of standard human performance than earlier human perceptual and oculomotor studies that typically used a small number of highly practiced human or nonhuman primate subjects.

Many previous behavioral studies have found that under a wide range of conditions, pursuit sensitivity to both low-level factors like speed and direction and high-order factors like windowing, depth interpretation, and stimulus ambiguity mirrors that of perception. This is based on extensive shared neural processing within the extrastriate cortex. The study described above capitalized on that fact and utilized a highly randomized stimulus environment (unpredictable onset time, speed, and direction) and a large pool of naïve participants with no training effects so as to minimize nonvisual influences, such as prediction and practice, to generate a robust archive of human dynamic visual motion processing for perception and oculomotor control. Accordingly, the set of oculometric measures provides valid, reliable, and robust estimates of several independent aspects of visual motion processing, which may prove useful as a clinical assessment tool for detecting and characterizing disorders or impairment of sensorimotor processing.

Use of Smooth-Pursuit Tasks for Clinical Screening

The quantitative metrics fulfill the basic criteria necessary for a useful psychometric test. Because the 180 trial test can be performed in a 15 minute session using only a chin rest, a noninvasive eye tracker, and a standard display system, some embodiments may provide a valuable new clinical assessment tool for detecting and characterizing visual pathology or impairment. First, the quantitative metrics are highly stable across repeated measurements. The metrics typically revealed substantial differences across subjects, with much smaller test-retest variability within subjects across sessions. To be an effective clinical screening tool, test-retest variability should be significantly smaller than the variability associated with a factor of interest (e.g., variability across clinical or display conditions). Second, the quantitative metrics detect impaired motion processing. Using a coarsely sampled motion stimulus that is known to produce degraded motion percepts, the metrics showed significant effects of sampling rate that were more pronounced at higher speed. Third, a correlation analysis of the set of 10 metrics revealed two statistically unrelated groups of metrics: one small group comprised of the amplitude and anisotropy of pursuit direction-tuning, and one larger group containing the remaining eight metrics with modest, albeit significant, correlations. Across the population, all metrics showed a significant degree of statistical independence from all other metrics, with the shared variance being on average only 23%. All of the oculometrics above were uncorrelated with both subject age and visual acuity, which is the standard measure of static visual processing.

The multidimensional metrics may not only be useful in detecting deficits in visual processing, but also in characterizing oculomotor signs of various disease states by showing a characteristic pattern in the changes across the 10 metrics. For a degenerative retinal disease such as retinitis pigmentosa, for example, prolonged pursuit latency and sluggish acceleration may be expected, as well as a high level of direction noise due to poor detection of motion onset in the periphery. However, the steady-state tracking metrics can be largely unimpaired when the target image falls on the intact fovea and tracking is driven by a higher-order target motion signal. For neurological conditions associated with diffuse damage to the extrastriate visual cortex (e.g., Alzheimer's disease, certain traumatic brain injuries, etc.) or degenerative disorders involving sensorimotor pathways, deficits in steady-state metrics may be expected, consistent with impaired higher-order visual perception.

Particular psychiatric or developmental disorders may yet show another characteristic pattern of deficits. In schizophrenia, for example, pursuit latency for 20 deg/s step-ramp motion has been reported to be 188 ms, similar to the observed median of 180 ms. However, the reported acceleration of 48 deg/s$^2$ and average gain of 0.36 are substantially lower than the observed median acceleration of 143 deg/s$^2$ and median gain of 0.82. If a patient has a severe motor deficit related to eye movements (e.g., square-wave jerk, oculomotor nerve palsy, etc.), the patient's oculomotor data in this paradigm may be so compromised as to be useless, or may show a characteristic impairment pattern in the data that masks possible concurrent dynamic visual impairments.

To evaluate the utility of the screening test for any particular pathological state quantitatively, its sensitivity should be estimated (i.e., the signal-to-noise ratio) for detecting disease using oculomotor symptoms. This relates to the psychometric concepts of validity, which address the signal, and test-retest reliability, which addresses the noise. For example, consider using a single metric (e.g., steady-state pursuit gain) as a tool to screen for mild traumatic brain injury (mTBI). A single gain measurement would have low sensitivity (i.e., low signal-to-noise ratio) if either the noise is large or the signal available to be measured is small. The noise component includes session-to-session variability in gain measurements for individual subjects (see graphs 200 of FIG. 2), as well as interobserver variability in the gain measurements across the normal and mTBI populations (see FIGS. 2-4).

The signal component results from the magnitude of the change in gain associated with various levels of mTBI, which should be large relative to the noise for any valid screening test for mTBI. Thus, by extension, the clinical utility can be quantified by determining the sensitivity (i.e., the signal-to-noise ratio) of the multidimensional set of metrics with respect to a particular factor of interest (e.g., mTBI). In other words, this can be quantified by statistically comparing the difference between the 10 metrics from a clinical population to their values in a normal population.

By using a multidimensional test, both the sensitivity for detecting any particular magnitude change can be measured in the standard signal-detection theory sense and a 10-dimensional direction change can be generated as a means of characterizing the type of impairment. Thus, the multidimensionality of the metric set both increases overall sensitivity and provides a qualitative advantage over single-metric tests by providing both a magnitude and direction for the impairment. This allows measurement of both impaired and better-than-normal dynamic visual processing.

For decades, gross oculomotor function has provided neurologists with a window to assess lesions and brain disease. Indeed, one of the earliest clinical oculomotor experiments used Raymond Dodge's photographic technique to measure horizontal smooth-pursuit eye movements in patients with several types of psychiatric disorders. See R. Dodge, "Five Types of Eye Movement in the Horizontal Meridian Plane of the Field of Regard," American Journal of Physiology, 8(2), pp. 307-327 (1903). Recent reports highlight the possible use of more quantitative metrics derived from standardized eye-movement tasks for more fine-tuned detection, screening, diagnostic uses, or to evaluate therapeutic interventions. As a practical matter, standardization of oculomotor tasks, saccade-detection algorithms, eye tracker calibration methods, and data analysis techniques may enable more rigorous quantitative screening and assessment of clinical conditions, for example, the presence or absence of deficits, the efficacy of a therapeutic intervention, or recovery from trauma. In particular, the multidimensional vector space of metrics described herein may allow for the identification of oculometric phenotypes of neural pathologies as represented by their characteristic vector displacement between the normal and pathological populations.

FIG. 6 is a flowchart illustrating a process for quantitatively analyzing visual performance, according to an embodiment of the present invention. The process begins with displaying a tracking target at an initial location on a display for a randomized delay interval at 610. After the randomized delay interval has elapsed, the tracking target is moved in a step to a random location on the display at 620. The movement Next, the tracking target is moved on the display towards the initial location at least until the tracking target crosses the initial location at 630. User eye position is periodically measured at 640 while the user is following the tracking target.

If more iterations are desired at 650, steps 620-640 are repeated. If there are no more iterations, the user eye response measurements are analyzed at 660 to determine a plurality of quantitative performance measurements. The results of the analysis are output at 670 to a display, in the form of a transmitted stream of data, stored in memory, or any other suitable output.

FIG. 7 is a block diagram of a computing system 700 configured to perform oculometric assessment, according to an embodiment of the present invention. Computing system 700 includes a bus 705 or other communication mechanism for communicating information, and processor(s) 710 coupled to bus 705 for processing information. Processor(s) 710 may be any type of general or specific purpose processor, including a central processing unit ("CPU") or application specific integrated circuit ("ASIC"). Processor(s) 710 may also have multiple processing cores, and at least some of the cores may be configured to perform specific functions. Multi-parallel processing may be used in some embodiments. Computing system 700 further includes a memory 715 for storing information and instructions to be executed by processor(s) 710. Memory 715 can be comprised of any combination of random access memory (RAM), read only memory (ROM), flash memory, cache, static storage such as a magnetic or optical disk, or any other types of non-transitory computer-readable media or combinations thereof. Additionally, computing system 700 includes a communication device 720, such as a transceiver and antenna, to wirelessly provide access to a communications network.

Non-transitory computer-readable media may be any available media that can be accessed by processor(s) 710 and may include both volatile and non-volatile media, removable and non-removable media, and communication media. Communication media may include computer-readable instructions, data structures, program modules or other data in a modulated data signal such as a carrier wave or other transport mechanism and includes any information delivery media.

Processor(s) 710 are further coupled via bus 705 to a display 725, such as a Liquid Crystal Display (LCD), for displaying information to a user. A keyboard and cursor control device 730, such as a computer mouse, are further coupled to bus 705 to enable a user to interface with computing system. However, in certain embodiments such as those for mobile computing implementations, a physical keyboard and mouse may not be present, and the user may interact with the device solely through display 725 and/or a touchpad (not shown). Any type and combination of input devices may be used as a matter of design choice. An eye tracker 735 provides measurements of user eye position.

Memory 715 stores software modules that provide functionality when executed by processor(s) 710. The modules include an operating system 740 for computing system 700. The modules further include a COBRA module 745 that is configured to analyze measurements of user eye movements. Computing system 700 may include one or more additional functional modules 750 that include additional functionality.

One skilled in the art will appreciate that a "system" could be embodied as an embedded computing system, a personal computer, a server, a console, a personal digital assistant (PDA), a cell phone, a tablet computing device, or any other suitable computing device, or combination of devices. Presenting the above-described functions as being performed by a "system" is not intended to limit the scope of the present invention in any way, but is intended to provide one example of many embodiments of the present invention. Indeed, methods, systems and apparatuses disclosed herein may be implemented in localized and distributed forms consistent with computing technology, including cloud computing systems.

It should be noted that some of the system features described in this specification have been presented as modules, in order to more particularly emphasize their implementation independence. For example, a module may be implemented as a hardware circuit comprising custom very large scale integration ("VLSI") circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Further, modules may be stored on a computer-readable medium, which may be, for instance, a hard disk drive, flash device, RAM, tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

The process steps performed in FIG. 6 may be performed by a computer program, encoding instructions for the nonlinear adaptive processor to perform at least the process described in FIG. 6, in accordance with embodiments of the present invention. The computer program may be embodied on a non-transitory computer-readable medium. The computer-readable medium may be, but is not limited to, a hard disk drive, a flash device, a random access memory, a tape, or any other such medium used to store data. The computer program may include encoded instructions for controlling the nonlinear adaptive processor to implement the process described in FIG. 6, which may also be stored on the computer-readable medium.

The computer program can be implemented in hardware, software, or a hybrid implementation. The computer program can be composed of modules that are in operative communication with one another, and which are designed to pass information or instructions to display. The computer program can be configured to operate on a general purpose computer, or an ASIC.

It will be readily understood that the components of various embodiments of the present invention, as generally described and illustrated in the figures herein, may be arranged and designed in a wide variety of different configurations. Thus, the detailed description of the embodiments of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A system, comprising:
a computing system including a display, the computing system configured to display a tracking target on the display; and
an eye tracker configured to take periodic measurements of eye position of a user based on the displayed tracking target position wherein
the computing system is further configured to:
receive the periodic measurements from the eye tracker,
mark an onset of pursuit movement using the periodic measurements from the eye tracker, and analyze the received periodic measurements to determine a plurality of quantitative performance measurements and display the eye position measurements and/or results of the analysis, or transmit the received periodic measurements to another computing system that analyzes the received periodic measurements to determine the plurality of quantitative performance measurements, and
output results of the analysis,
wherein the plurality of quantitative performance measurements comprises at least one metric for quantifying vigor of pursuit initiation and at least one metric for quantifying a quality of steady-state tracking, and
wherein the vigor of pursuit initiation comprises an acceleration metric that measures initial pursuit acceleration following pursuit initiation by the user, the acceleration determined starting at the onset of pursuit movement as marked.

2. The system of claim 1, wherein the plurality of quantitative measurements comprises direction tuning, speed tuning, or any combination or subset thereof.

3. The system of claim 1, wherein the at least one metric for quantifying the vigor of the pursuit initiation quantifies latency and acceleration, and the at least one metric for quantifying the quality of the steady-state tracking quantifies gain, saccade amplitude, and a proportion of smooth movement.

4. The system of claim 1, wherein the metrics for quantifying vigor of pursuit initiation and quantifying the quality of steady-state tracking provide a baseline for the same user to determine deviation from normal performance for the user.

5. The system of claim 1, wherein the metrics for quantifying vigor of pursuit initiation and quantifying the quality of steady-state tracking provide a measurement of user performance against a reference population of performance metrics from normal human subjects to determine a deviation from normal for the user.

6. The system of claim 1, wherein the metrics for quantifying vigor of pursuit initiation and quantifying the quality of steady-state tracking provide a measurement of peripheral vision, prediction, asymmetry between eye performance, or any combination thereof, to determine at least one of: a type and a degree of brain injury, a progression of or recovery from disease, whether the user is faking an injury, whether the user is consciously failing to perform the task, or whether the user is intoxicated.

7. The system of claim 1, wherein the metrics for quantifying vigor of pursuit initiation and quantifying the quality of steady-state tracking provide a baseline measurement from the same user for an injury to determine whether the user is faking the injury.

8. The system of claim 1, further comprising:
comparing, by the computing system, the metrics for quantifying vigor of pursuit initiation and quantifying the quality of steady-state tracking against previous measurements for the user to determine whether the user is improving, deteriorating, or remaining the same.

9. A system, comprising:
a computing system including a display, the computing system configured to display a tracking target on the display; and
an eye tracker configured to take periodic measurements of eye position of a user based on the displayed tracking target position, wherein
the computing system is further configured to:
receive the periodic measurements from the eye tracker,
analyze the received periodic measurements to determine a plurality of quantitative performance measurements and display the eye position measurements and/or results of the analysis, or transmit the received periodic measurements to another computing system that analyzes the received periodic measurements to determine the plurality of quantitative performance measurements, and
output results of the analysis, and
wherein the plurality of quantitative performance measurements comprise a cloverleaf shaped function as a measure of the user's own idiosyncratic oblique effect, and
the computing system further configured to provide a pattern uniquely identifying the user using the cloverleaf shaped function.

10. The system of claim 9, wherein the cloverleaf shaped function as a measure of the user's own idiosyncratic oblique effect provides a baseline for the same user to determine deviation from normal performance for the user.

11. The system of claim 9, wherein the cloverleaf shaped function as a measure of the user's own idiosyncratic oblique effect provides a measurement of user performance against a reference population of performance metrics from normal human subjects to determine a deviation from normal for the user.

12. The system of claim 9, wherein the cloverleaf shaped function as a measure of the user's own idiosyncratic oblique effect provides a measurement of peripheral vision, prediction, asymmetry between eye performance, or any combination thereof, to determine at least one of: a type and a degree of brain injury, a progression of or recovery from disease, whether the user is faking an injury, whether the user is consciously failing to perform the task, or whether the user is intoxicated.

13. The system of claim 9, wherein the cloverleaf shaped function as a measure of the user's own idiosyncratic oblique effect provides a baseline measurement from the same user for an injury to determine whether the user is faking the injury.

14. The system of claim 9, further comprising:
comparing, by the computing system, a previous cloverleaf shaped function for the user to a current cloverleaf shaped function to determine whether the user is improving, deteriorating, or remaining the same.

15. A non-transitory computer-readable medium storing a computer program, the program configured to cause at least one processor to:
execute a randomized tracking task by moving a tracking target;
receive a plurality of eye position measurements tracking a user's following of the tracking target over time;
analyze the plurality of eye position measurements to determine a plurality of quantitative metrics, or transmit the plurality of eye position measurements to a remote computing system to analyze the plurality of eye position measurements and determine the plurality of quantitative metrics; and
based on the plurality of quantitative metrics, provide determination of whether the user has a brain injury, whether the user has a disease, whether the user is faking an injury, whether the user is intoxicated, or any combination thereof, wherein
the plurality of quantitative performance metrics comprise a direction of pursuit response, and a fitting function to describe a shape of a cloverleaf shaped function is determined by $$f(\varphi) = 1 + \alpha \cdot \cos(4(\varphi + \Delta)) - \beta \cdot \cos(2(\varphi + \Delta))$$

where $\alpha$ describes a magnitude of cardinal-oblique anisotropy, $\beta$ describes asymmetry between a size of vertical and horizontal lobes, and $\Delta$ describes an orientation of the cloverleaf shaped function.

16. The non-transitory computer-readable medium of claim 15, wherein the direction of pursuit response provides a baseline for the same user to determine deviation from normal performance for the user.

17. The non-transitory computer-readable medium of claim 15, wherein the direction of pursuit response provides a measurement of user performance against a reference population of performance metrics from normal human subjects to determine a deviation from normal for the user.

18. The non-transitory computer-readable medium of claim 15, wherein the direction of pursuit response provides a measurement of peripheral vision, prediction, asymmetry between eye performance, or any combination thereof, to determine at least one of: a type and a degree of brain injury, a progression of or recovery from disease, whether the user is faking an injury, whether the user is consciously failing to perform the task, or whether the user is intoxicated.

19. The non-transitory computer-readable medium of claim 15, wherein the direction of pursuit response provides a baseline measurement from the same user for an injury to determine whether the user is faking the injury.

20. The non-transitory computer-readable medium of claim 15, further comprising:
comparing, by the computing system, the direction of pursuit response against previous measurements for the user to determine whether the user is improving, deteriorating, or remaining the same.

* * * * *